United States Patent [19]

Swenson

[11] Patent Number: 5,494,657
[45] Date of Patent: Feb. 27, 1996

[54] SKIN CARE FORMULATION

[76] Inventor: Russell H. Swenson, 1360 Persimmon Dr., St. Charles, Ill. 60174

[21] Appl. No.: 270,701

[22] Filed: Jul. 5, 1994

Related U.S. Application Data

[63] Continuation of Ser. No. 876,657, Apr. 30, 1992, abandoned.

[51] Int. Cl.$^6$ .......................................................... A61K 7/42
[52] U.S. Cl. .............................. 424/59; 514/846; 514/847
[58] Field of Search ..................................... 514/846, 847; 424/59

[56] References Cited

U.S. PATENT DOCUMENTS

| | | | |
|---|---|---|---|
| 4,164,564 | 8/1979 | Chen | 424/677 |
| 4,671,955 | 6/1987 | Palinczar | 424/59 |
| 4,683,134 | 7/1987 | Palinczar | 424/59 |
| 4,847,072 | 7/1989 | Bissett et al. | 514/724 |
| 5,139,784 | 8/1992 | Ciaudelli | 424/401 |

OTHER PUBLICATIONS

Amoco Chemical Co., Bulletin HB-1c, Oct. 1987.
Amoco Chemical Co., Bulletin HB-3c, 1991.
Amoco Chemical Co., Bulletin HB-4d, 1991.
Amoco Chemical Co., Bulletin 12-M, 1990.

*Primary Examiner*—Shean C. Wu
*Attorney, Agent, or Firm*—McDermott, Will & Emery

[57] ABSTRACT

The invention comprises compositions for lubricating skin comprising petrolatum, at least one of a squalene or hydrogenated polybutene, non-hydrogenated polybutene, a natural or synthetic source of at least one of a fatty acid or fatty acid ester and an anti-oxidant. The compositions are particularly useful in moisturizing or lubricating compromised or traumatized skin and protecting skin from trauma due to exposure to ultraviolet radiation, radiation therapy and chemotherapy.

10 Claims, No Drawings

SKIN CARE FORMULATION

This is a continuation of application Ser. No. 07/876,657, filed on Apr. 30, 1992, now abandoned.

FIELD OF THE INVENTION

This invention relates to compositions and methods for moisturizing skin. More particularly, the invention relates to compositions which are useful in moisturizing traumatized or compromised skin and in protecting skin from trauma due to exposure to harsh conditions such as ultraviolet radiation, radiation therapy and chemotherapy.

BACKGROUND OF THE INVENTION

Many current skin care products such as lotions and cosmetics are water-based. Such products are normally formulated with anti-bacterial components or preservatives to prevent the formation of bacteria which could cause infection on the skin. While the anti-bacterial components are necessary to prevent bacterial contamination, they may cause chemical irritation to the skin. It would therefore be advantageous to provide a non-water-based skin care composition which has an excellent moisturizing ability with no requirement for water or anti-bacterial components.

It would be also advantageous to provide a skin care formulation that is similar to natural sebum, which is the natural oil on the skin provided by sebaceous glands. Such a skin care formulation would be particularly advantageous where the skin has been traumatized or compromised and natural sebum production is impaired, such as skin which is damaged by radiation or chemotherapy.

Further, with the rise in new cases of skin cancer and premature aging of the skin, which are attributed in part to excessive exposure to the sun's damaging rays, it would be highly desirable to provide moisturizing skin care formulations containing sunscreen active agents.

In U.S. Pat. Nos. 4,671,955 and 4,683,134, there are disclosed water-proof sunscreen compositions. U.S. Pat. No. 4,671,955 discloses compositions comprising ethyl hydroxyethylcellulose polymers, an active sunscreen agent, and optionally water-insoluble emollients, suspended particulate matter, volatile liquid carriers, thickening agents, fragrance oil and liquified propellent. U.S. Pat. No. 4,683,134 similarly discloses water-proof sunscreen compositions comprising monohydric alcohols, sunscreen agents, ethylcellulose, an acrylic acid cross-linked polymer and an alkaline neutralizing agent. Neither of the above-referenced patents discloses a skin care formulation similar to natural sebum.

It is therefore an object of the present invention to provide skin care compositions which are not water-based and require no anti-bacterial components. It is another object to provide skin care compositions which are similar to natural sebum. It is yet another object of the invention to provide skin care compositions and methods of treatment using these compositions which will moisturize compromised or traumatized skin such as the skin of chemotherapy or radiation therapy patients. Finally, it is an object of the present invention to provide compositions which provide effective protection from the damaging effects of ultraviolet radiation.

SUMMARY OF THE INVENTION

The invention is a composition for lubricating skin comprising:
a) from about 55 to about 75 weight percent petrolatum;
b) from about 5 to about 35 weight percent of at least one of a squalene or hydrogenated polybutene;
c) from about 1 to about 15 weight percent of a non-hydrogenated polybutene;
d) from about 0.5 to about 5 weight percent of a natural or synthetic source of at least one of a fatty acid or fatty acid ester; and
e) from about 0.0005 to about 3.0 weight percent of an anti-oxidant.

The invention also comprises methods of making the above composition comprising mixing about 55 to about 75 weight percent petrolatum; about 5 to about 35 weight percent of at least one of a squalene or hydrogenated polybutene; about 1 to about 15 weight percent of a non-hydrogenated polybutene; about 0.5 to about 5 weight percent of a natural or synthetic source of at least one of a fatty acid or fatty acid ester; and about 0.0005 to about 3.0 weight percent of an anti-oxidant.

The invention further comprises methods of lubricating skin comprising applying the composition of the invention directly onto the skin.

DETAILED DESCRIPTION OF THE INVENTION

The invention is a composition for lubricating skin comprising petrolatum, at least one of a squalene or hydrogenated polybutene, non-hydrogenated polybutene, a natural or synthetic source of at least one of a fatty acid or fatty acid ester and an anti-oxidant.

Petrolatums which are useful in the invention are any of a purified mixture of semisolid or liquid hydrocarbons suitable as a base for topical pharmaceuticals and cosmetics. These are mainly of the methane series of the general formula $C_nH_{2n+2}$. They are generally yellowish to light amber or white and practically odorless and tasteless. Examples of suitable petrolatums include petroleum jelly, paraffin jelly, vasoliment, liquid paraffin, mineral oil, white mineral oil and paraffin oil. One preferred commercially available petrolatum which can be used in this invention is sold under the name AMOJELL® by Amoco Oil Company, Chicago, Ill.

The polybutenes (both hydrogenated and non-hydrogenated) useful in this invention are viscous butylene polymers which are called polybutenes in the trade, but are more correctly termed polybutylenes. The hydrogenated forms are made by hydrogenation of polybutylenes, and preferably have molecular weights of between about 200 and about 2000 and most preferably between about 250 and about 500. Such hydrogenated polybutenes are commercially available from Amoco Chemical Company in three molecular weights under the designations L-14E (also called Panalane®), H-25E and H-300E. These are bright, clear viscous liquids which do not readily oxidize and contain no cyclic compounds. They are miscible with a variety of mineral oils and organic solvents and are hydrophobic but can be easily emulsified. Amoco L-14E is especially preferred because it feels much like the luxury cosmetic ingredient squalene (found in large quantities in shark liver oil) but costs much less and does not require endangering natural sources such as sharks for its manufacture. More detailed information regarding Amoco L-14E, H-25E and H-300E is contained in Amoco Chemical Company Bulletins HB-2d, HB-3c and HB-4d, Amoco Chemical Company, Chicago, Ill. (1991), which is incorporated by reference herein. The natural squalene material can be substituted for the synthetic hydrogenated polybutenes described herein, but this would be much more costly.

The unsaturated, non-hydrogenated polybutenes useful in the invention are those having a molecular weight of between about 200 and about 2000. Most preferred are polybutenes having a molecular weight of between about 250 and about 500. Examples of non-hydrogenated polybutenes include L-14, L-50, L-100, H-15, H-25, H-35, H-50, H-100, H-300, H-1500 and H-1900, all available from Amoco Chemical Company, Chicago, Ill. One preferred commercially available non-hydrogenated polybutene is sold under the designation L-50 (also called INDOPOL®) by Amoco Chemical Company, Chicago, Ill. This polybutene has a molecular weight of 420 (number average, vapor phase osmometry, $M_n$) a specific gravity of 845–860 (ASTM D1298 at 15.5° C.) a kinematic viscosity of 106–112 (ASTM D445, at 38° C., cSt), and a flash point of 138° C. min. (Cleveland open cup, ASTM D92). More detailed information regarding such non-hydrogenated polybutenes is contained in Amoco Chemical Company Bulletin No. 12-M, Amoco Chemical Company (1990), incorporated by reference herein.

The source of at least one of a fatty acid or fatty acid ester such as stearic, oleic or palmitic acids useful in this invention can be any natural source such as animal, fish and vegetable fats and oils. These can also be prepared synthetically as by hydrogenation of cottonseed and other vegetable oils (stearic acid), or by separation from olive oil by double fractionation (oleic acid). One especially preferred natural source of stearic, oleic and palmitic acids useful in this invention is cod liver oil. Cod liver oil is an excellent source of glycerides of palmitic, stearic and oleic acids (approximately 19% saturated fatty acids, remainder unsaturated) and also provides an excellent source of Vitamins A and D. It also has the added benefits of being a source of cholesterol and a source of omega 3 fatty acid.

Anti-oxidants which are useful in the invention include anti-oxidants suitable for application to skin which are well known in the cosmetics and skin care arts. Examples of suitable anti-oxidants include natural or synthetic alpha-tocopherol or Vitamin E. Alpha-tocopherol is especially preferred because it is readily available in synthetic form or from inexpensive natural sources such as wheat germ, corn, sunflower seed, rapeseed, soybean oils, alfalfa and lettuce. It is freely soluble in oil and provides a natural odor remover for the otherwise odorous cod liver oil.

Fragrances and sunscreens suitable for cosmetic applications which are well known in the art can also be added to the skin care formulations of the invention. Fragrances are optionally added to the compositions of the invention in very low amounts such as less than one percent. One preferred commercially available fragrance useful in the invention is designated Fragrance #4401 from Belle-Aire Fragrances, Inc. of Mundelein, Ill.

Sunscreens are generally added to the compositions of the invention in higher levels varying from about 3–15% depending on the desired Sun Protection Factor (SPF). Such sunscreens or ultraviolet absorbers include octyl methoxycinnamate, octyl dimethyl PABA, dihydroxyacetone, benzophenone-1, -2, -3, or -4, octyl salicylate, homosalate, cinoxate, 2-phenyl-5-benzimidazole-sulfonic acid, and digalloyl trioleate. Two sunscreens which are especially preferred for use in the invention are benzophenone-3 (oxybenzone) and octyl methoxycinnamate.

Without wishing to be bound by any particular theory, it is believed that the polybutenes in the skin care formulation of the invention provide an occlusive barrier to the skin care formulation, and the source of at least one of a fatty acid or fatty acid ester, such as cod liver oil, attracts oxygen from the atmosphere causing some permeability of this occlusive barrier. In this manner, the skin care formulation offers a barrier function or protection from harsh conditions in the atmosphere, while at the same time maintaining some permeability of oxygen which promotes healthy skin. The anti-oxidant ingredient, such as alpha-tocopherol, seems to provide some balance to the barrier function and oxygen permeability function by reducing the amount of oxygen which would normally be attracted to the source of fatty acid or fatty acid ester such as the cod liver oil ingredient. Therefore, the invention provides a balanced formulation which protects the skin while allowing controlled oxygen permeability.

Other aspects and advantages of the invention will become apparent from the following examples, which are intended to illustrate, but not limit, the practice of the invention.

EXAMPLE 1

A preferred composition of the invention was made by mixing the ingredients listed in Table 1.

TABLE 1

| Ingredient | % By Weight | % By Vol. |
| --- | --- | --- |
| Petrolatum | 71.34 | 71.21 |
| Hydrogenated Polybutene | 18.59 | 19.0 |
| Non-hydrogenated Polybutene | 7.13 | 7.12 |
| Fatty Acid Source (Cod Liver Oil) | 2.60 | 2.37 |
| Fragrance | 0.34 | 0.30 |
| Anti-oxidant (Alpha-tocopherol) | 0.003 | 0.003 |

The ingredients were mixed by first heating the petrolatum (AMOJELL®, Amoco Oil Company, Chicago, Ill.) to at least 130° F. but not more than 150° F. The hydrogenated polybutene (L-14E, PANALANE®, Amoco Chemical Company, Chicago, Ill.) and the non-hydrogenated polybutene (L-50, INDOPOL®, Amoco Chemical Company, Chicago, Ill.), both polybutenes being at about room temperature or approximately 70° F., were added and stirred for about ten minutes.

Next, the source of fatty acid or fatty acid ester (cod liver oil) and anti-oxidant (alpha-tocopherol) were mixed together and heated to about 130°–135° F. These were then added slowly along with the fragrance (#4401, Belle-Aire Fragrances, Inc.) into the petrolatum and polybutene mixture while stirring and maintaining the temperature of the mixture at about 130° to 150° F. The mixture was then poured into appropriate size containers such as one or two ounce jars or three ounce squeeze tubes.

EXAMPLE 2

A sunscreen product was also made according to the invention. The sunscreen formulation is set forth in Table 2.

TABLE 2

| Ingredient | % By Weight | % By Vol. |
| --- | --- | --- |
| Petrolatum | 61.84 | 63.08 |
| Hydrogenated Polybutene | 18.59 | 19.34 |
| Non-hydrogenated Polybutene | 7.13 | 7.76 |
| Fatty Acid Source (Cod Liver Oil) | 2.60 | 2.42 |

TABLE 2-continued

| Ingredient | % By Weight | % By Vol. |
|---|---|---|
| Fragrance | 0.34 | 0.30 |
| Anti-oxidant (Alpha-tocopherol) | 0.003 | 0.003 |
| Sunscreen Agent (Parsol MCX) | 7.00 | 6.00 |
| Sunscreen Agent (Uvinul M-40) | 2.50 | 1.60 |

The sunscreen formula was made according to the procedure described in Example 1, except that the sunscreen ingredients (Parsol MCX and Uvinul M-40 manufactured by Givaudan Corp., Clifton, N.J. and BASF, Wyandotte, Mich., respectively) were added one at a time to the total mixture while maintaining the temperature of the mixture at about 130°–150° F.

EXAMPLE 3

The composition described in Example 1 was applied to traumatized areas of the skin of several cancer patients who had undergone radiation therapy. Excellent responses to the skin care compositions were found, including relief from discomfort and improvement of traumatized areas.

The skin care compositions of the invention have several advantages. First, they do not require any water or anti-bacterial components. Second, the compositions are similar to natural sebum and therefore provide natural lubrication of skin. Third, the compositions are easily and inexpensively manufactured. Fourth, the skin care compositions of the invention provide excellent sunscreen formulations. Fifth, the skin care compositions appear to be particularly useful for traumatized or compromised skin. Of course, there are numerous other advantages which will be apparent to those skilled in the art.

What is claimed is:

1. A skin care composition for moisturizing compromised or traumatized skin comprising:
   a) from about 55 to about 75 weight percent petrolatum;
   b) from about 5 to about 35 weight percent of at least one of a squalene or hydrogenated polybutene;
   c) from about 1 to about 15 weight percent of a non-hydrogenated polybutene;
   d) from about 0.5 to about 5 weight percent of a natural or synthetic source of at least one of a fatty acid or fatty acid ester; and
   e) from about 0.0005 to about 3.0 weight percent of an anti-oxidant.

2. The composition of claim 1 wherein the hydrogenated and non-hydrogenated polybutenes each have a molecular weight of from about 200 to about 2000.

3. The composition of claim 1 wherein the hydrogenated and non-hydrogenated polybutenes each have a molecular weight of from about 200 to about 500.

4. The composition of claim 1 wherein the source of fatty acid or fatty acid ester comprises cod liver oil.

5. The composition of claim 1 wherein the anti-oxidant comprises a natural or synthetic alpha-tocopherol.

6. The composition of claim 1 additionally comprising a sunscreen agent.

7. The composition of claim 1 additionally comprising a fragrance.

8. A composition for lubricating compromised or traumatized skin comprising:
   a) from about 55 to about 75 weight percent petrolatum;
   b) from about 5 to about 35 weight percent of at least one of a squalene or hydrogenated polybutene;
   c) from about 1 to about 15 weight percent of a non-hydrogenated polybutene;
   d) from about 0.5 to about 5 weight percent of cod liver oil; and
   e) from about 0.0005 to about 3.0 weight percent of a natural or synthetic alpha-tocopherol.

9. A method of making a skin care composition for moisturizing compromised or traumatized skin comprising mixing about 55 to about 75 weight percent petrolatum which has been heated to about 130° to about 150° F. with about 5 to 35 weight percent of at least one of a squalene or hydrogenated polybutene; about 1 to about 15 weight percent of a non-hydrogenated polybutene; about 0.5 to about 5 weight percent of a natural or synthetic source of at least one of a fatty acid or fatty acid ester; and about 0.0005 to about 3.0 weight percent of an anti-oxidant.

10. A method of lubricating skin comprising applying directly onto the skin the composition of claim 1 in an amount effective to lubricate the skin.

\* \* \* \* \*